United States Patent [19]
Hall et al.

[11] Patent Number: 5,876,390
[45] Date of Patent: Mar. 2, 1999

[54] ABSORBENT ARTICLES, SUCH AS A DIAPER, A PANTS-TYPE DIAPER, AN INCONTINENCE GUARD, A SANITARY NAPKIN OR LIKE ARTICLE

[75] Inventors: Benny Hall, Gothenburg; Ingela Ternström, Mölnlycke, both of Sweden

[73] Assignee: SCA Hygiene Products AB, Gothenburg, Sweden

[21] Appl. No.: 513,791

[22] PCT Filed: Mar. 4, 1994

[86] PCT No.: PCT/SE94/00188

§ 371 Date: Aug. 29, 1995

§ 102(e) Date: Aug. 29, 1995

[87] PCT Pub. No.: WO94/20056

PCT Pub. Date: Sep. 15, 1994

[30] Foreign Application Priority Data

Mar. 5, 1993 [SE] Sweden .................................. 9300736

[51] Int. Cl.[6] .................................................... A61F 13/15
[52] U.S. Cl. .......................................... 604/385.2; 604/378
[58] Field of Search ..................................... 604/358, 378, 604/385.1, 385.2, 386, 373

[56] References Cited

U.S. PATENT DOCUMENTS

| | | | |
|---|---|---|---|
| 4,425,129 | 1/1984 | Karami | 604/385.2 |
| 4,692,163 | 9/1987 | Widlund et al. | 604/385.2 |
| 4,775,375 | 10/1988 | Aledo | 604/385.2 |
| 4,808,177 | 2/1989 | DesMarais et al. | |
| 4,842,596 | 6/1989 | Kielpikowski et al. | |
| 4,897,084 | 1/1990 | Ternstrom et al. | 604/385.2 |
| 4,998,929 | 3/1991 | Björksund et al. | 604/385.2 |
| 5,026,364 | 6/1991 | Robertson | 604/385.2 |
| 5,037,415 | 8/1991 | Leroy et al. | |
| 5,087,255 | 2/1992 | Sims | 604/385.2 |
| 5,129,893 | 7/1992 | Thoren | 604/385.2 |
| 5,366,453 | 11/1994 | Zehner et al. | 604/385.2 |
| 5,397,318 | 3/1995 | Dreier | 604/385.2 |

FOREIGN PATENT DOCUMENTS

| | | |
|---|---|---|
| 0219326 | 4/1987 | European Pat. Off. . |
| 0311333 | 4/1989 | European Pat. Off. . |
| 0398392 | 11/1990 | European Pat. Off. . |
| 0532035A2 | 3/1993 | European Pat. Off. . |
| 1561021 | 2/1980 | United Kingdom . |
| 2243327A | 10/1991 | United Kingdom . |
| 2263622A | 8/1993 | United Kingdom . |
| WO 90/04374 | 5/1990 | WIPO . |
| WO 93/12746 | 7/1993 | WIPO . |

*Primary Examiner*—Mark O. Polutta
*Attorney, Agent, or Firm*—Burns, Doane, Swecker & Mathis LLP

[57] ABSTRACT

The present invention relates to an absorbent article (1), such as a diaper, a pants-type diaper, an incontinence guard, a sanitary napkin or like article, comprising an absorbent body (2) of generally elongated shape and having two mutually opposing end-edges (7, 8) and two mutually opposing side edges (9, 10); a liquid-permeable top sheet (3) which is placed on one side of the absorbent body (2) and which is intended to lie proximal to the wearer in use, and a liquid-impermeable bottom sheet (4) placed on the other side of the absorbent body (2). The inventive article is characterized in that longitudinally extending elastic elements (25–28), for instance bands, threads or the like, are mounted across the absorbent body (2) close to respective side-edges (9, 10); and in that the elastic elements are firmly joined to the absorbent body (2) and entrain the body in the regions around the elastic elements (25–28) to form leakage barriers.

20 Claims, 3 Drawing Sheets

5,876,390

ABSORBENT ARTICLES, SUCH AS A DIAPER, A PANTS-TYPE DIAPER, AN INCONTINENCE GUARD, A SANITARY NAPKIN OR LIKE ARTICLE

BACKGROUND OF THE INVENTION

The present invention relates to an absorbent article, such as a diaper, a pants-type diaper, an incontinence guard, a sanitary napkin or like article comprising an absorbent body having a generally elongated shape with two mutually opposing end-edges and two mutually opposing side-edges; a fluid-permeable top sheet placed on that side of the absorbent body which lies proximal to the wearer in use and a Fluid-impermeable bottom sheet which is placed on the opposite side of the absorbent body; and longitudinally extending elastic elements, such as bands or threads, are mounted over the absorbent body in a pre-tensioned state close to respective side-edges.

One problem which can readily occur when using such articles as diapers, pants-type diapers or incontinence guards of the aforesaid kind is that urine and loose faeces are liable to leak from the article and soil and wet clothes, bed linen, etc. Such leakage occurs particularly in the region of the wearer's legs, since the article is narrowest in the region of the article which is intended to be placed between the legs of the wearer and since the fluid discharged by the wearer is normally delivered within this part of the article. Various types of barriers disposed at the sides of the absorbent article have been proposed with the intention of counteracting such leakage. For instance, patent publication EP 0,219,326 discloses such a side leakage guard which has the form of elastically contractile, longitudinally extending barrier flaps which have a distal end which are intended to lift from the top sheet of the article in response to the effect of elastic devices at this end, so as to form a barrier against the flow of loose faeces past the side-edges of the absorbent article.

Another example of side leakage guards is described in EP 0,311,333. One part of the top sheet has an upstanding region in which an elastic device is arranged in a manner which enables the device to move in the crotch part of the article and force the upstanding region to stand-up and therewith distance itself from an underlying layer, for instance the absorbent body. It is said that one of the purposes of the side leakage guard is to cause the elastic device to "move" in a manner to "find" the wearer's groin and form a durable, effective seal against the wearer's skin, since the elastic device is able to move freely and adapt to the wearer's body.

One problem with earlier known side leakage guards is that the free elastic in the outer edge of the barrier can chafe the crotch of the wearer. The combination of chafing and urine can result in irritation of the skin. It is essential that chafing from elastication is avoided in those regions in which the wearer's skin is subjected to the effect of urine over long periods.

Another problem with leakage barriers that are comprised solely of thin layers is that the barrier is liable to bend outwards and therewith fail to provide any real protection against leakage.

Still another problem is that it is necessary for the thin barriers to be made impervious if they are to protect against large lateral leakage flows, therewith incurring the risk that the article becomes excessively impervious and preventing the skin of the wearer within the confines of the leakage barriers from breathing in a satisfactory manner.

OBJECTS AND SUMMARY

The present invention provides leakage barriers with which all of the aforesaid problems are eliminated. An absorbent article of the kind defined in the introduction is characterized in that the elastic elements extend inwardly along each respective side-edge (9,10) of the absorbent body (2) and are firmly joined to the absorbent body in the crotch part of the article, so that when the elastic elements contract, the absorbent body accompanies the elastic elements in the regions around the elastic elements to form leakage barriers.

Because the longitudinally extending elastic elements are effectively anchored in the absorbent body, the absorbent material accompanies and is lifted-up by the elastic in the region therealong, so as to form soft, leakage-preventing barriers or walls. Since the elastic elements are accompanied by and "embedded" in the soft absorbent body, the wearer's skin is not subjected to chafing.

The barrier walls formed by the elastic are shape-stable in use, i.e. the barriers will not be folded to one side as in the case of the earlier known, thin barriers and will provide positive protection against leakage.

The barrier walls may be air-permeable and because of their width fluid is unable to pass readily therethrough.

The invention will now be described in more detail with reference to exemplifying embodiments thereof and also with reference to the accompanying drawings.

DETAILED DESCRIPTION OF PREFERRED EMBODIMENTS

Figure 1:
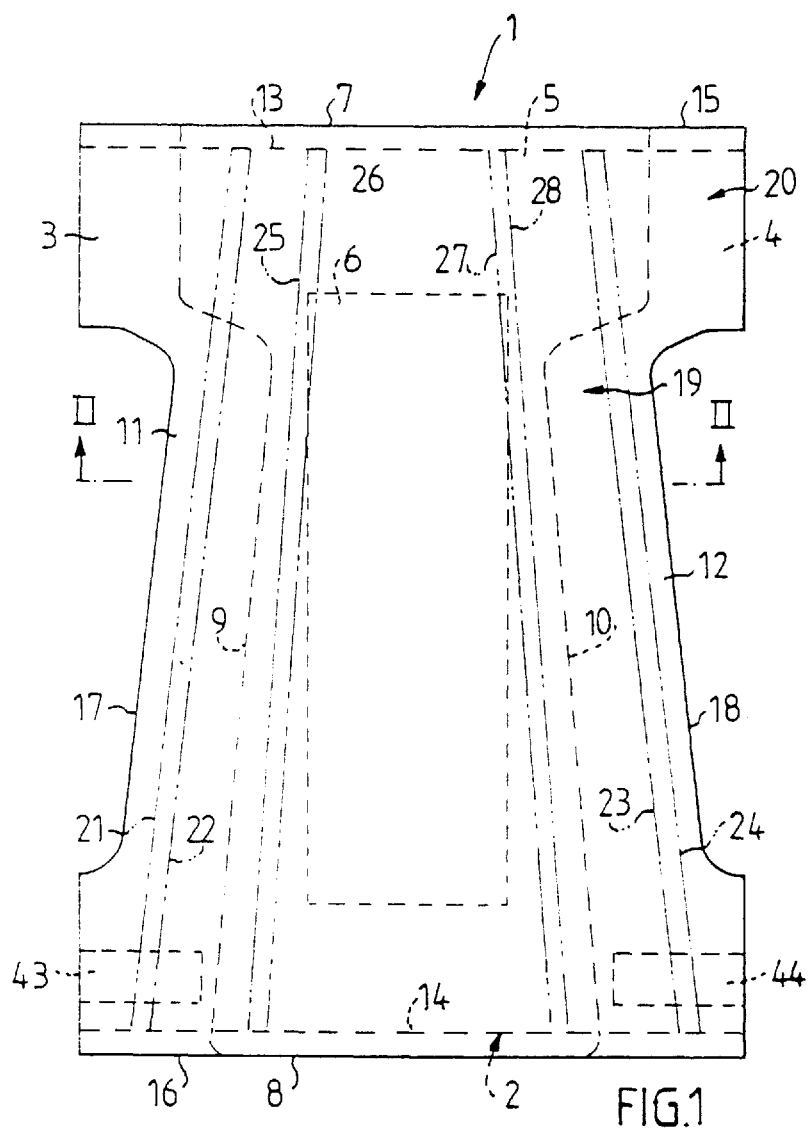
FIG. 1 is a top view of an inventive diaper with that side of the diaper which lies proximal to the wearer in use facing towards the viewer and shows all elastic elements stretched from a relaxed state.
Figure 2:
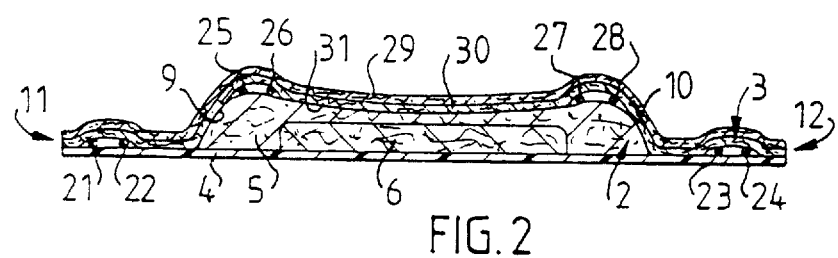
FIG. 2 is a cross-sectional view of the diaper shown in FIG. 1, said view being taken on the line II—II in FIG. 1.
Figure 3:
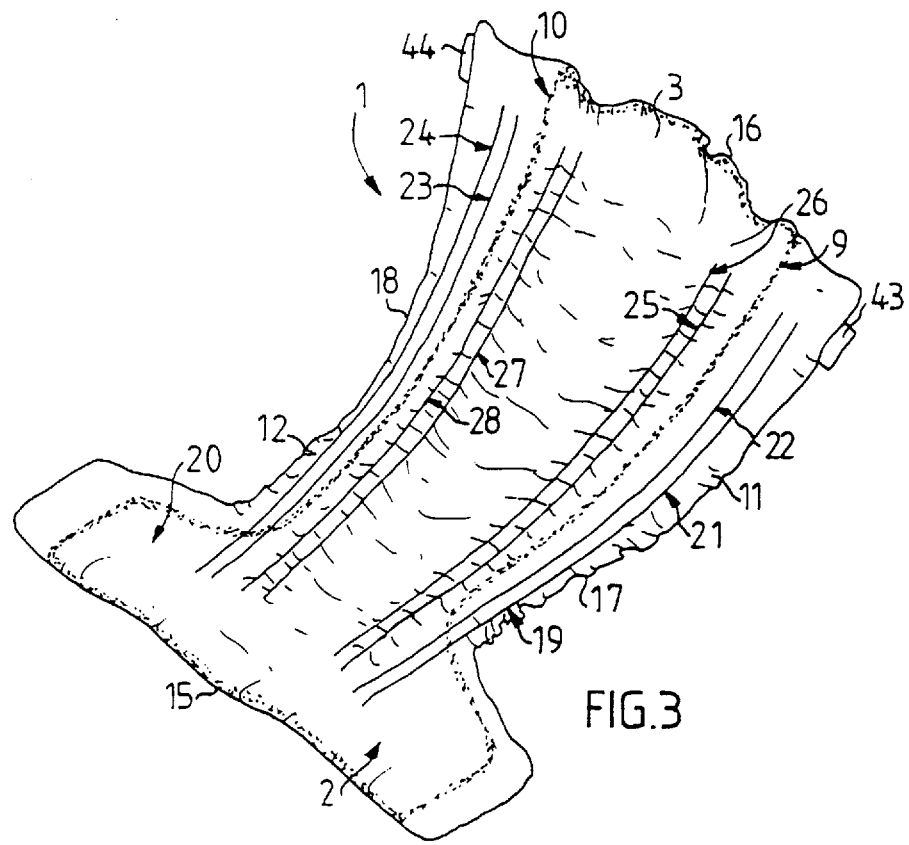
FIG. 3 is a perspective view of the diaper shown in FIG. 1, with the elastic elements partially contracted.

Shown in FIGS. 1–3 is a diaper 1 which comprises an absorbent body 2, a liquid-permeable top sheet 3 which is placed on that side of the body 2 which is proximal to the wearer in use and which in FIGS. 1 and 3 faces towards the viewer, and a liquid-impermeable bottom sheet 4 which is placed on the other side of the absorbent body 2. The absorbent body 2 has a generally elongated shape, with two mutually opposing end-edges 7, 8 and two mutually opposing side-edges 9, 10. The absorbent body 2 is comprised of two absorbent layers 5, 6, an upper, T-shaped absorbent layer 5 proximal to the top sheet 3, and a lower rectangular absorbent layer 6. The T-shaped upper absorbent layer 5 is larger than the lower rectangular absorbent layer 6 and has the same length as the diaper 1. The top sheet 3 and the bottom sheet 4 have generally the same T-shape as the T-shaped absorbent layer 5, although the top and bottom sheets project laterally beyond the side-edges 9, 10 of the absorbent body and are mutually joined at these protruding parts such as to form flexible side flaps 11, 12. The diaper has no corresponding end flaps, and the bottom sheet 4 is, instead, folded around the end-edges 7, 8 of the absorbent body 2 and extends slightly in over the absorbent body 2, beneath the top sheet 3. The folded end-edges of said parts are indicated by respective broken lines 13, 14, which extend parallel with respective end-edges 15, 16 of the diaper. The top sheet 3 has the same longitudinal extension as the absorbent body 2.

Two first elastic elements 21–24 are mounted in each of the side flaps 11, 12 and extend from the rear end-edge 16 of the diaper along the side-edges 17, 18 thereof, up to the diaper crotch part 19, i.e. the narrowest part of the diaper which, when the diaper is worn, is intended to lie between the wearer's legs. In the front part 20 of the diaper, forwardly of the crotch part 19, the first elastic elements 21–24 extend in over the transverse parts of the T-shaped absorbent layer 5 and terminate in the proximity of the front end-edge 15 of the diaper.

The two first elastic elements 21–24 extend parallel with one another in respective side flaps 11, 12 and have a linear extension. The elements 21–24 also follow generally the side-edges 9, 10 of the T-shaped absorbent layer and also the diaper side-edges 17, 18 in the crotch part 19 of the diaper. Since the side-edges 9, 10 of the absorbent layer and the diaper side-edges 17, 18 converge in a direction towards the front part 20 within the diaper crotch part 19, the pairs of first elastic elements 21–24 will converge in the same direction, even though they never meet at the front end-edge 15 of the diaper.

Two second elastic elements 25–28 extend along respective side-edges 9, 10 of the absorbent body 2 generally parallel with the first elastic elements 21–24 and inwardly of said respective side-edges 9, 10, i.e. as seen in a direction towards the centre of the absorbent body 2. These two pairs of second elastic elements are mutually parallel and have a linear extension, precisely as the first elastic elements 21–24. The second elastic elements 25–28 extend from a region in the proximity of the rear end-edge 16 of the diaper along respective side-edges 9, 10 of the absorbent body 2, up to a region in the proximity of the front end-edge 15 of the diaper, constantly over a region of the upper T-shaped absorbent layer 5 of said absorbent body. Since the pairs of second elastic elements 25–28 are parallel with respective adjacent first elastic elements 21–24 on the same longitudinally extending diaper half, the pairs of second elastic elements 25–28 will also converge in a direction towards the front-part 20 of the diaper. However, the pairs of second elastic elements 25–28 will not meet in the front-part 20 of the diaper.

Disposed on a diaper rear-part 42 are adhesive fastener tabs 43, 44, one on each side edge 17, 18. The fastener tabs 43, 44 may be of any known kind of fastener means which function to join the front part 20 to the rear part 42 on respective sides of the diaper when the diaper is worn.

The absorbent body 2 comprises typical absorbent material, for instance cellulose fibres, viscose fibres or superabsorbent, synthetic polymers, such as cross-linked polyacrylates. Naturally, mixtures of different absorbent materials can also be used. The absorbent body 2 may also include non-absorbent material, for instance thermoplastic binding fibres. The T-shaped upper absorbent layer 5 and the rectangular absorbent layer 6 may differ mutually with regard to density, thickness, surface weight, choice of absorbent material, and so on. One or more parameters may also vary within one and the same absorbent layer. It will also be understood that the absorbent body 2 may consist of fewer or more than two absorbent layers.

As will be understood, the sheet or sheets may also have a shape different to that shown in FIGS. 1–3, for instance an hourglass shape. Neither is it necessary for the absorbent layers to have different shapes, but may have mutually the same shape and may also be of mutually the same size. The upper absorbent layer 5 may also consist of generally non-absorbent fibres, although preferably fibres which have been made hydrophilic, for instance polyethylene, polypropylene or polyester fibres or mixtures thereof. The fibres may be bonded to form a wadding-like structure, which may be treated with a wetting agent so as to enable the structure to receive liquid more readily.

The top sheet 3 is comprised of two liquid-permeable surface layers 29–30, i.e. a first surface layer 29 which faces the wearer in use, and a second surface layer 30 disposed between the first surface layer 29 and the absorbent body 2. It is also conceivable for the diaper to include only one surface layer, i.e. said surface layer alone forms the top sheet 3, or the top sheet 3 may include more than two surface layers. The first and the second surface layers 29, 30 may, for instance, be comprised of non-woven material, perforated plastic film, for instance polyethylene film, or some other liquid-permeable material.

The bottom sheet 4 is conveniently comprised of a liquid-impervious layer of polyethylene film or the like. This liquid-impervious layer may be air or vapour permeable, so as to enhance wearer comfort.

The first and the second elastic elements 21–28 may, for instance, consist in elastic bands or threads which are mounted in a pre-tensioned state. It is also possible to use elastic films, non-woven material and the like. It is also conceivable to use elastic elements which need not be pre-tensioned in order to act elastically in the diaper. In the embodiment illustrated in FIGS. 1–3, the elastic elements have been mounted in pairs. It will be understood, however, that single elastic elements or more than two elastic elements may be used together instead. It is also conceivable to mount the elastic elements in a non-parallel and non-linear pattern, without deviating from the concept of the present invention, provided that the second elastic elements 25–28 constantly extend over parts of the absorbent body without any part of said elements extending beyond respective side-edges 9–10 of the absorbent body. The second elastic elements 25–28 are firmly joined to the absorbent body 2 by means of a network-pattern of binding agent. The top sheet 3 is also firmly joined to the absorbent body 2 by means of the same binding agent pattern. In this way, the side-parts of the absorbent body will form soft walls which are raised by the second elastic elements 25–28 as said elements contract, as will best be seen from FIG. 3. Thus, the absorbent body 2 accompanies the second elastic elements 25–28 as they strive to contract when the diaper is curved around the wearer's body, and the relatively soft absorbent pad will alleviate the chafing effect that sharp, uplifted folds or flaps could otherwise have when elastic elements are permitted to act in said flaps, in accordance with what has earlier been mentioned with regard to prior art techniques.

In the embodiment illustrated in FIGS. 1–3, the first surface layer 29 is firmly joined to the second surface layer 30, whereas the second surface layer 30 and the second elastic elements 25–28 are firmly joined to the uppermost T-shaped absorbent layer 5 of the absorbent body. The contact surface 31 of the absorbent body 2 bordering on the second surface layer 30 is comprised of the surface of the T-shaped absorbent layer 5 and is thus comprised of bonded or non-bonded fibres, depending on whether or not the absorbent layer 5 has been bonded in some way or another. When the absorbent layer 5 exhibits a bonded structure, the extent to which the layer is bonded can vary in many ways, for instance by mixing-in different quantities of binding fibres or by compressing the absorbent layer under different conditions, such as pressure and moisture content.

The internal coherent strength of an absorbent fibre structure of fluff pulp will be sufficient to take-up the normal stresses that occur as the pre-tensioned elastic contracts. The binding agent pattern, which also penetrates slightly into the fibre structure, assists in increasing the strength of the fibre structure and spreading the stresses from the elastic. A suitable binding agent pattern is achieved by applying the binding agent in a thin layer which cracks into a net-like binding pattern when applied.

However, when a highly tensioned elastication is desired, it is appropriate to amplify the fibre structure with thermoplastic fibres capable of forming a coherent network structure through the absorbent body.

Figure 4:
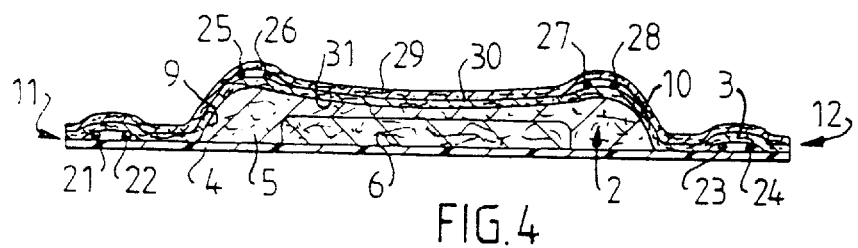
FIG. 4 is a cross-sectional view of an alternative embodiment of the diaper shown in FIG. 1, said view being taken on the line II—II in FIG. 1.

FIG. 4 is a cross-sectional view of an alternative diaper embodiment which is identical to the embodiment illustrated in FIGS. 1–3 with the exception that the second elastic elements 25–28 are disposed between the first and the second surface layers 29–30. The surface layers 29–30 and the second elastic elements 25–28 are, in other respects, mutually joined in the same way as that described with reference to FIGS. 1–3.

In another embodiment, not shown, the absorbent body includes a reinforcing layer which extends over at least the side of the absorbent body facing towards the top sheet. For instance, a tissue layer or a layer of non-woven material may cover the whole of the absorbent body, so as to enhance its coherency or for other process/technical reasons. In this case, the contact surface of the absorbent body facing the top sheet is comprised of a surface of the reinforcing layer.

Figure 5:
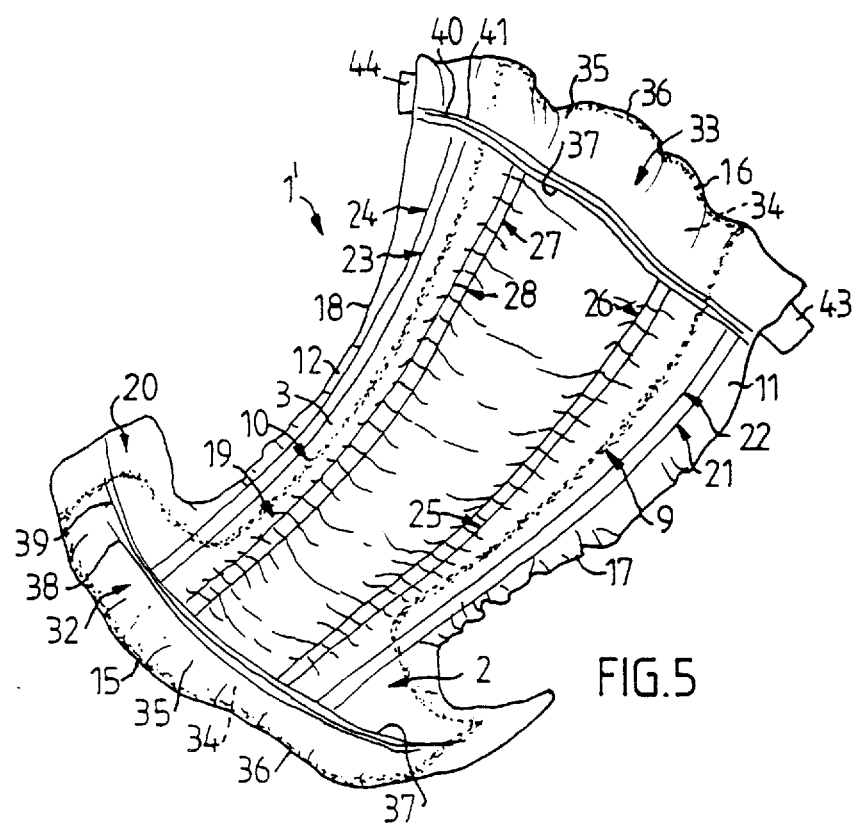
FIG. 5 is a perspective view of another embodiment of an inventive diaper, and shows the elastic elements partially contracted.

FIG. 5 illustrates a further exemplifying embodiment in which barrier flaps 32, 33 are arranged transversely across a diaper 1' in the proximity of the diaper end-edges 15, 16, said diaper being identical to the diaper of FIGS. 1–3 in other respects. Each of the barrier flaps 32, 33 has an inner surface 34 which extends in towards the diaper, and an outer surface 35 which extends outwardly from the diaper, a fixed edge 36 and a free edge 37. Two elastic devices 38–41 are mounted along the free edge 37 of respective barrier flaps 32, 33 and act on the barrier flaps 32, 33 in a manner to enable the free edge 37 of respective barrier flaps 32, 33 to lift from the surface of the top layer 3, thereby enabling a pocket to form between the inner surface 34 of respective barrier flaps and the top sheet 3 at respective end-edges 15, 16 of the diaper. The elastic devices may consist of the same kind of elastic material as the first and the second elastic elements 21–28. The barrier flaps 32, 33 may be comprised of a fold in the top sheet 3 or of a strip of liquid-permeable or liquid-impermeable material attached separately to the top sheet.

It will be understood that the invention is not restricted to the illustrated exemplifying embodiments and that several modifications can be made within the scope of the following Claims.

The modern, so-called pants-type diapers, may also be provided with leakage barriers in accordance with the invention. This also applies to sanitary napkins, with which the proof against leakage can be improved with barriers according to the invention.

The absorbent body 2 may be comprised of a unit which remains coherent under the stresses that occur in use, such as a unit made from an absorbent foam material or in the form of a fibre layer reinforced with thermoplastic fibres.

The article may also be provided with elastic elements which are also connected to the absorbent body in the vicinity of the end-edges thereof and extend transversely across the body.

We claim:

1. An absorbent article comprising:
    an absorbent body which has a generally elongated shape with two mutually opposing end-edges and two mutually opposing side-edges, said absorbent body defining an absorbent body proximal to a wearer in use;
    a liquid-permeable top sheet on a side of the absorbent body which is proximal to the wearer in use;
    a liquid-impermeable bottom sheet on another side of the absorbent body; and
    longitudinally extending elastic elements mounted between the top sheet and the absorbent body in a pre-tensioned state extending along each respective side-edge of the absorbent body inwardly of said side-edges as seen in a direction towards the center of the absorbent body and are joined to the absorbent body for a predetermined distance in at least a crotch part of the article, such that when the elastic elements contract, the absorbent body accompanies the elastic elements within the predetermined distance, in the regions around said elastic elements, to form leakage barriers of a predetermined length.

2. An absorbent article according to claim 1, wherein the elastic elements are mounted between the top sheet and a binding agent pattern which bonds the top sheet and the elastic elements to the absorbent body.

3. An absorbent article according to claim 2, wherein the top sheet includes two liquid-permeable surface layers made, for instance, of non-woven material, in that the elastic elements are mounted between a first of said surface layers and a binding agent pattern which bonds the first surface layer and the elastic elements to a second surface layer; and in that the second surface layer (30) is joined to the absorbent body.

4. An absorbent article according to claim 1, wherein the absorbent body includes at least one fibre layer; and in that the contact surface of the absorbent body bordering on the top sheet is comprised of a surface of one of said fibre layers.

5. An absorbent article according to claim 4, wherein the fibre layer whose surface borders on the top sheet includes cellulose fibres, viscose fibres or other absorbent fibres or mixtures thereof.

6. An absorbent article according to claim 4, wherein the fibre layer whose surface borders on the top sheet includes non-absorbent fibres.

7. An absorbent article according to any one of claim 1, wherein the absorbent body includes a reinforcing layer, which extends over at least that side of the absorbent body which faces the top sheet; and in that the contact surface of the absorbent body facing towards the top sheet is comprised of a surface of said reinforcing layer.

8. An absorbent article according to claim 1, wherein the elastic elements are comprised of a plurality of mutually parallel elastic threads.

9. An absorbent article according to claim 1, wherein the absorbent body, at least in a layer joined with the elastic elements, is comprised of a unit which will retain its coherency when subjected to the stresses that occur in use, said unit having the form of an absorbent foam material or the form of a fibre layer reinforced with thermoplastic fibres.

10. An absorbent article according to claim 1, wherein a barrier flap extends transversely across the article in the proximity of at least one end-edge of said article, said barrier flap having an inner side which faces inwardly towards the article and an outer side which faces outwardly away from the article and which also includes elastic means whose elastic contraction force is operative in raising the barrier flap so as to form a pocket between the inner side of the barrier flap and the top sheet at said end-edge.

11. An absorbent article according to claim 1, wherein elastic elements joined to the absorbent body are also mounted in the vicinity of the end-edges of the absorbent body and extend transversely across said body.

12. An absorbent article according to claim 1, wherein the elastic elements are firmly joined to the absorbent body.

13. An absorbent article according to claim 1, wherein the elastic elements are directly joined to the absorbent body.

14. An absorbent article according to claim 3, wherein the nonwoven material is perforated plastic.

15. An absorbent article according to claim 6, wherein the nonabsorbent fibres have been made hydrophilic.

16. An absorbent article according to claim 6, wherein the nonabsorbent fibres are polypropylene.

17. An absorbent article according to claim 6, wherein the nonabsorbent fibres are polyester.

18. An absorbent article according to claim 6, wherein the nonabsorbent fibres are a mixture of polypropylene and polyester.

19. An absorbent article according to claim 7, wherein the reinforcing layer is a tissue layer.

20. An absorbent article according to claim 7, wherein the reinforcing layer is a nonwoven material.

* * * * *